United States Patent
Alderete, Jr. et al.

(10) Patent No.: US 8,870,818 B2
(45) Date of Patent: Oct. 28, 2014

(54) SYSTEMS AND METHODS FOR ALIGNMENT AND DETECTION OF A CONSUMABLE COMPONENT

(71) Applicant: Medtronic MiniMed, Inc., Northridge, CA (US)

(72) Inventors: Juan M. Alderete, Jr., Granada Hills, CA (US); R. Marie Tieck, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 79 days.

(21) Appl. No.: 13/678,245

(22) Filed: Nov. 15, 2012

(65) Prior Publication Data
US 2014/0135692 A1    May 15, 2014

(51) Int. Cl.
*A61M 5/50* (2006.01)
*G01R 33/00* (2006.01)
*A61M 39/02* (2006.01)

(52) U.S. Cl.
CPC ............. *A61M 5/5086* (2013.01); *G01R 33/00* (2013.01); *A61M 2039/0267* (2013.01)
USPC .. 604/111; 604/538; 324/750.16; 324/750.24

(58) Field of Classification Search
CPC ................... A61M 25/0158; A61M 2005/172; A61M 2039/0267; A61M 2039/1022; A61M 2205/60; A61M 2206/6054; G01R 33/00; G01R 33/0005; G01R 33/0041; G01R 33/0047
USPC ......... 604/533, 538, 905; 324/750.16, 750.24
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

PCT Search Report (PCT/US02/03299), Oct. 31, 2002, Medtronic Minimed, Inc.

(Continued)

*Primary Examiner* — Quynh-Nhu H Vu
(74) *Attorney, Agent, or Firm* — Ingrassia Fisher & Lorenz, P.C.

(57) ABSTRACT

Systems and methods for alignment and detection of a consumable component are disclosed herein. For example, a method for determining if a consumable component is coupled to a durable component to enable dispersion of a medicine is provided. The method includes determining if a signal from an electrical contact coupled to a durable component has changed an electrical state, and comparing the signal to a reference signal from a second electrical component coupled to the durable component. The method includes sampling a sensor coupled to the durable component to acquire sensor data indicative of a magnetic field observed by the sensor, and outputting data that a consumable component is coupled to the durable component if the signal is different than the reference signal, and the sensor data is within an acceptable range.

4 Claims, 7 Drawing Sheets

(56) References Cited

U.S. PATENT DOCUMENTS

| | | |
|---|---|---|
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |

(56) References Cited

U.S. PATENT DOCUMENTS

| | | |
|---|---|---|
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,828,764 B2 | 11/2010 | Moberg et al. |
| 7,905,868 B2 | 3/2011 | Moberg et al. |
| 2001/0044731 A1 | 11/2001 | Coffman et al. |
| 2002/0013518 A1 | 1/2002 | West et al. |
| 2002/0055857 A1 | 5/2002 | Mault |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0077081 A1* | 3/2008 | Mounce et al. ............ 604/67 |
| 2008/0154503 A1 | 6/2008 | Wittenber et al. |
| 2008/0269687 A1 | 10/2008 | Chong et al. |
| 2009/0081951 A1 | 3/2009 | Erdmann et al. |
| 2009/0082635 A1 | 3/2009 | Baldus et al. |
| 2009/0299290 A1 | 12/2009 | Moberg |
| 2011/0160654 A1* | 6/2011 | Hanson et al. ............ 604/67 |
| 2011/0160655 A1* | 6/2011 | Hanson et al. ............ 604/67 |
| 2011/0160666 A1 | 6/2011 | Hanson et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting A Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting A Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII] With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

Strowig S M (1993). Initiation and Management of Insulin Pump Therapy. The Diabetes Educator, vol. 19, No. 1, pp. 50-60.

Walsh J, et al. (1989). Pumping Insulin: The Art of Using an Insulin Pump. Published by MiniMed•Technologies.

(Intensive Diabetes Management, 1995). Insulin Infusion Pump Therapy. pp. 66-78.

Disetronic My Choice™ D-TRON™ Insulin Pump Reference Manual. (no date).

Disetronic H-TRON® plus Quick Start Manual. (no date).

Disetronic My Choice H-TRONplus Insulin Pump Reference Manual. (no date).

(56) References Cited

OTHER PUBLICATIONS

Disetronic H-TRON®plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jonsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

(56) References Cited

OTHER PUBLICATIONS

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

SYSTEMS AND METHODS FOR ALIGNMENT AND DETECTION OF A CONSUMABLE COMPONENT

TECHNICAL FIELD

Embodiments of the subject matter described herein relate generally to fluid infusion devices for delivering a medication fluid to the body of a user. More particularly, embodiments of the subject matter relate to systems and methods for the alignment and detection of a consumable component, such as a base plate for use with a fluid infusion device.

BACKGROUND

Certain diseases or conditions may be treated, according to modern medical techniques, by delivering a medication or other substance to the body of a patient, either in a continuous manner or at particular times or time intervals within an overall time period. For example, diabetes is commonly treated by delivering defined amounts of insulin to the patient at appropriate times. Some common modes of providing insulin therapy to a patient include delivery of insulin through manually operated syringes and insulin pens. Other modern systems employ programmable fluid infusion devices (e.g., insulin pumps) to deliver controlled amounts of insulin to a patient.

A fluid infusion device suitable for use as an insulin pump may be realized as an external device or an implantable device, which is surgically implanted into the body of the patient. External fluid infusion devices include devices designed for use in a generally stationary location (for example, in a hospital or clinic), and devices configured for ambulatory or portable use (to be carried by a patient).

In certain instances, the devices configured for portable use can include multiple components that cooperate to deliver the insulin to the patient. For example, the device can include a consumable, generally single use, component and a durable, repeated use, component. In one example, the consumable component can be coupled to the durable component to enable insulin delivery to the patient.

Accordingly, it is desirable to provide a system and method for the alignment and detection of a removable and replaceable consumable component that is couplable to a durable component to ensure proper insulin delivery. Furthermore, other desirable features and characteristics will become apparent from the subsequent detailed description and the appended claims, taken in conjunction with the accompanying drawings and the foregoing technical field and background.

BRIEF SUMMARY

Various embodiments of systems and methods for alignment and detection of a consumable component are provided here. For example, a method for determining if a consumable component is coupled to a durable component to enable dispersion of a medicine is provided. The method can include determining if a signal from an electrical contact coupled to a durable component has changed an electrical state, and comparing the signal to a reference signal from a second electrical component coupled to the durable component. The method can also include that if the signal is different than the reference signal, sampling a sensor coupled to the durable component to acquire sensor data indicative of a magnetic field observed by the sensor, and outputting data that a consumable component is coupled to the durable component if the signal is different than the reference signal, and the sensor data is within an acceptable range.

According to various exemplary embodiments, provided is a method for determining if a consumable component is coupled to a durable component to enable dispersion of a medicine. The method can include comparing a first signal from a first electrical contact coupled to the durable component and a second signal from a second electrical contact coupled to the durable component to a reference signal from a third electrical contact coupled to the durable component to determine if the consumable component has contacted the durable component. The method can also include if at least one of the first signal and the second signal has changed electrical state while the reference signal has remained substantially the same, sampling a sensor coupled to the durable component to acquire sensor data indicative of a magnetic field emitted by a magnetic source on the consumable component. The method can include comparing the acquired sensor data to calibrated sensor data, and outputting data that a consumable component is coupled to the durable component if at least one of the first signal and the second signal has changed electrical states and the acquired sensor data is within an acceptable range based on the calibrated sensor data.

Further provided according to various exemplary embodiments is a fluid infusion device for dispersion of a medicine. The fluid infusion device can include a consumable component including a source of a magnetic field, and a durable component. The durable component can include a first electrical contact, a second electrical contact and a third electrical contact. The first electrical contact and third electrical contact can have a first electrical state when the consumable component is spaced apart from the durable component and a second electrical state when the consumable component is coupled to the durable component. The durable component can include a sensor that observes the magnetic field emitted by the source. The fluid infusion device can also include a contact control module that receives a first signal that indicates if the first electrical contact and third electrical contact are in the first electrical state or the second electrical state, and a second signal from the second electrical contact. Based on the first signal and the second signal, the contact control module can set contact data that indicates if the consumable component is in contact with the durable component. The fluid infusion device can include an alignment control module that receives the contact data, and based on the contact data samples the sensor to acquire sensor data. The alignment control module can output connection data that indicates whether the consumable component is coupled to the durable component based on the contact data and the sensor data.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "first", "second", and other such numerical terms referring to structures do not imply a sequence or order unless clearly indicated by the context. Such terminology may include the words specifically mentioned above, derivatives thereof, and words of similar import.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

The following description relates to a fluid infusion device of the type used to treat a medical condition of a patient. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: United States patent application number 2009/0299290 A1; United States patent application number 2008/0269687; U.S. Pat. No. 7,828,764; and U.S. Pat. No. 7,905,868 (the entire content of these patent documents is incorporated by reference herein).

Figure 1:
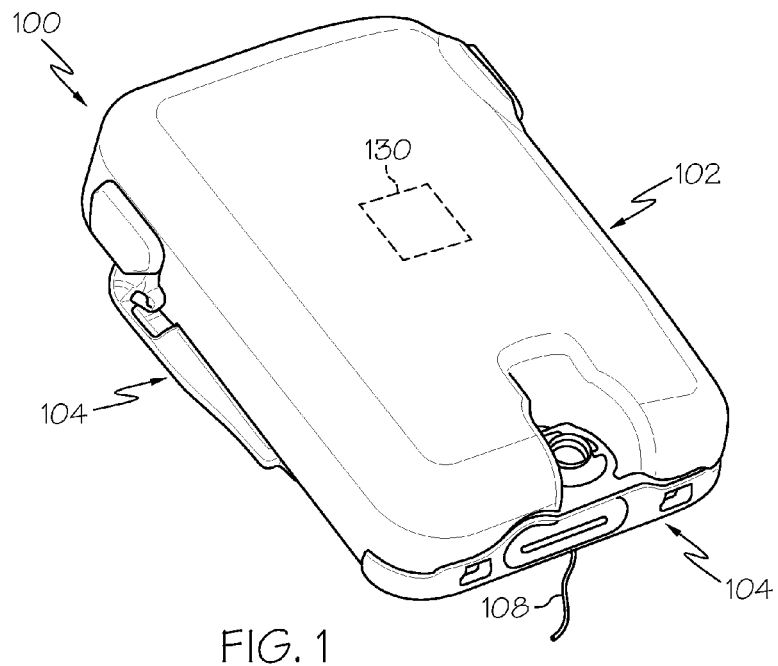
FIG. 1 is a perspective view of an exemplary embodiment of a fluid infusion device.
Figure 2:
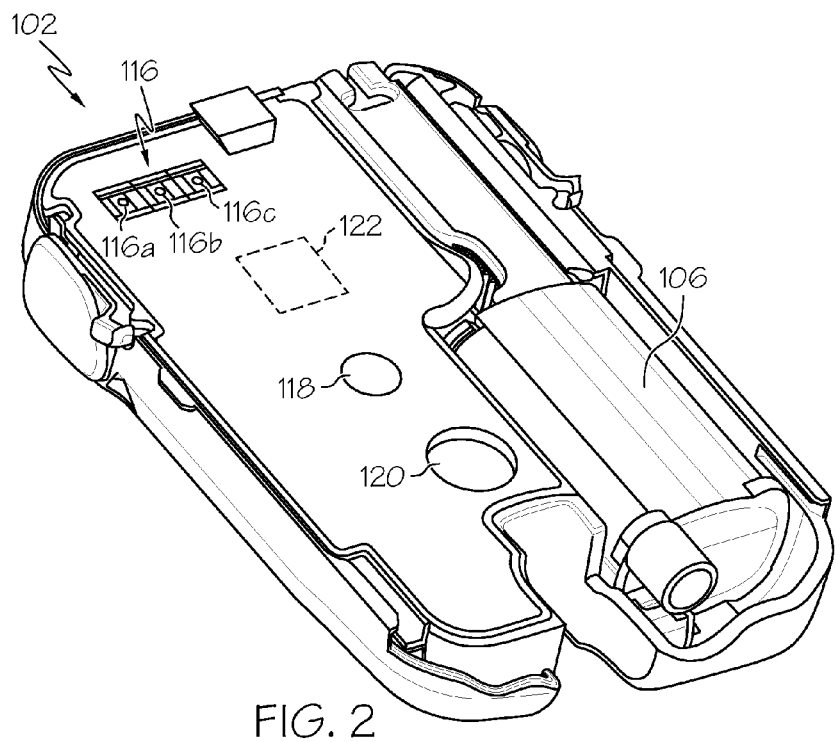
FIG. 2 is a perspective view of an exemplary durable housing of the fluid infusion device of FIG. 1.
Figure 3:
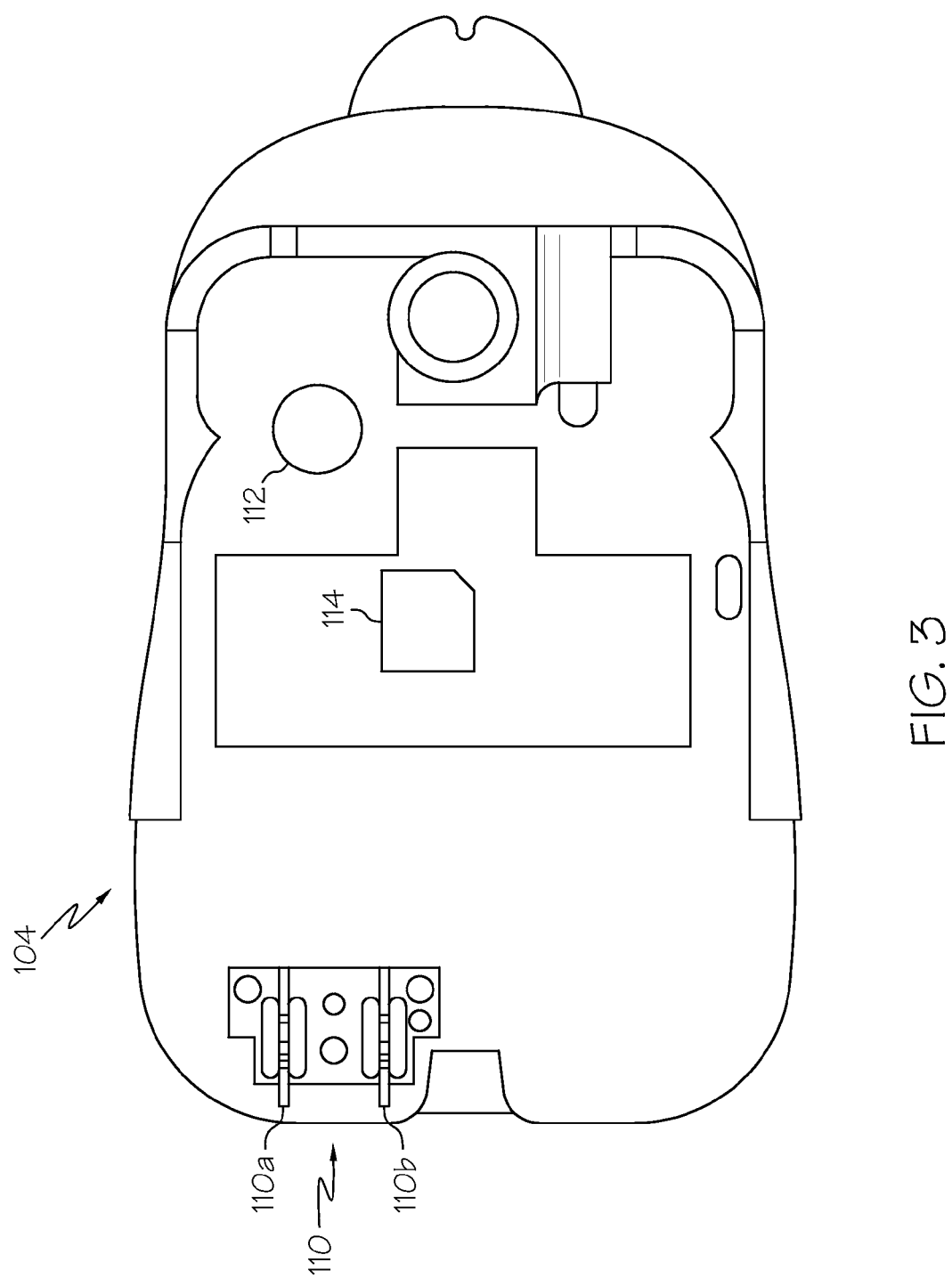
FIG. 3 is a perspective view of an exemplary base plate of the fluid infusion device of FIG. 1.

FIG. 1 is a perspective view of an exemplary embodiment of a fluid infusion device 100. In one example, the fluid infusion device 100 can include two primary components, which can be removably coupled to each other: a first durable component or durable housing 102 and a second consumable component or base plate 104, which is also shown in FIG. 3. It should be noted that although the housing 102 is described herein as being a durable, multiple use component, the housing 102 can be a consumable, single use component in certain embodiments. Similarly, although the base plate 104 is described herein as comprising a consumable, single use component, the base plate 104 can be a durable, multiple use component in certain embodiments. The fluid infusion device 100 can also include or cooperate with a removable/replaceable fluid reservoir 106 (FIG. 2). For the illustrated embodiment, the fluid reservoir 106 can mate with, and can be received by, the durable housing 102. Alternatively, the fluid reservoir 106 can mate with, and can be received by, the base plate 104. The fluid reservoir 106 can hold or store insulin, which can be dispensed with the fluid infusion device 100.

With continued reference to FIG. 1, FIG. 1 illustrates the durable housing 102 and the base plate 104 coupled together. The durable housing 102 and the base plate 104 are cooperatively configured to accommodate removable coupling of the durable housing 102 to the base plate 104. In practice, the durable housing 102 and/or the base plate 104 can include features, structures, or elements to facilitate removable coupling (e.g., pawls, latches, rails, slots, keyways, buttons, or the like). The removable nature of the durable housing 102 enables the patient to replace the fluid reservoir 106 as needed. Moreover, the durable housing 102 can be removed (while leaving the base plate 104 adhered to the patient) to allow the patient to swim, shower, bathe, and participate in other activities that might otherwise damage or contaminate the durable housing 102. When the durable housing 102 is removed from the base plate 104, the fluid flow path is broken, and the base plate 104 will appear as shown in FIG. 3.

With continued reference to FIG. 3, the base plate 104 is shown in greater detail. The base plate 104 can be temporarily adhered to the skin of the patient using, for example, an adhesive layer of material. After the base plate 104 is affixed to the skin of the patient, a suitably configured insertion device or apparatus may be used to insert a fluid delivery needle or cannula 108 (see FIG. 1) into the body of the patient. The cannula 108 can function as one part of the fluid delivery path associated with the fluid infusion device 100, as is well understood. With continued reference to FIG. 3, the base plate 104 can include a shorting mechanism 110, a first magnetic source 112 and a first magnetically attractive source 114.

The shorting mechanism 110 can cooperate with at least one electrical contact 116 coupled to or disposed on a portion of the durable housing 102 to enable the durable housing 102 to detect that the base plate 104 is coupled to the durable housing 102, as will be discussed in greater detail herein. In one example, with reference to FIG. 2, the durable housing 102 can include a first electrical contact 116a, a second electrical contact 116b and a third electrical contact 116c. It should be noted, however, that the durable housing 102 can include any suitable number of electrical contacts 116, which can cooperate with the shorting mechanism 110. The electrical contacts 116 can be made of any suitable material such as metal, a rubber conductive pad, as well as any other electrical conductor. The second electrical contact 116b can be made of the same material as the first electrical contact 116a and/or the third electrical contact 116c. In other embodiments, the second electrical contact 116b may be made of a different material (e.g., a different conductive material, or a non-conductive material) from the first electrical contact 116a and/or the third electrical contact 116c.

In addition, the second electrical contact 116b need not be limited to being arranged in between the first electrical contact 116a and third electrical contact 116c, but can also be arranged to be the outermost electrical contact in some embodiments. As such, the electrical contacts 116 (e.g., first electrical contact 116a, second electrical contact 116b and third electrical contact 116c) can be arranged or otherwise provided on the durable housing 102 in any suitable manner, for example linearly/non-linearly, equidistant/non-equidistant, similar/varying heights, arranged on similar/varying surfaces, same/different resistances, same/different materials, and/or the like. Further, in some embodiments, a bias member, such as a spring, or the like, may be provided to bias the electrical contacts 116 either individually, partially (e.g., some, but not all), or collectively toward a first position (e.g., an extended position). As such, the electrical contacts 116 may be moveable toward a second position (e.g., a retracted position), for example, as the durable housing 102 and the base plate 104 are brought together.

In some embodiments, the second electrical contact 116b can be arranged between the first electrical contact 116a and the third electrical contact 116c to prevent a false detection of a proper connection of the durable housing 102 and the base plate 104. For example, the durable housing 102 can distinguish between a case where a stray metal object (e.g., a metal key, paper clip, coin) or other electrical conductor contacts the first electrical contact 116a, the third electrical contact 116c, and the second electrical contact 116b as opposed to a proper connection where only the first electrical contact 116a and the third electrical contact 116c are contacted (by the shorting mechanism 110).

With reference to FIG. 3, in one exemplary embodiment, the shorting mechanism 110 can establish an electrical connection with the first electrical contact 116a and third electrical contact 116c in a case where the durable housing 102 and the base plate 104 are connected properly or otherwise brought into a pre-defined, sufficiently aligned position and/or in a pre-defined, sufficiently close proximity. The pre-defined aligned position and/or proximity, for example, can correspond to a properly aligned and mutually proximate position for connection of the durable housing 102 and the base plate 104 for operation. Generally, the shorting mechanism 110 can be composed of a suitable metallic material. Thus, when the shorting mechanism 110 is coupled to the first electrical contact 116a and third electrical contact 116c, the shorting mechanism 110 can complete a circuit formed the first electrical contact 116a, the third electrical contact 116c and the shorting mechanism 110. The resistance of the shorting mechanism 110 can be such that upon completion of this circuit, a voltage applied between the first electrical contact 116a and third electrical contact 116c can be measured or observed as a lower voltage signal than a voltage signal measured or observed when the base plate 104 is not attached.

In one example, the shorting mechanism 110 can include a first end 110a generally spaced apart from a second end 110b. In certain embodiments, the first end 110a and the second end 110b can contact the first electrical contact 116a and the third electrical contact 116c respectively when the durable housing 102 and the base plate 104 are connected properly, for example, as shown in FIG. 1. As such, the shorting mechanism 110 can contact the first electrical contact 116a and the third electrical contact 116c, but not the second electrical contact 116b. Suitable circuitry (not shown) connected to the electrical contacts 116 can detect an electrical connection or short between the first electrical contact 116a and the third electrical contact 116c (via the shorting mechanism 110) indicating a proper connection of the durable housing 102 and the base plate 104.

Furthermore, the electrical contacts 116 and/or the shorting mechanism 110 can be arranged on their respective parts such that in a case where the durable housing 102 and the base plate 104 are not properly connected, an electrical connection between the first electrical contact 116a and the third electrical contact 116c cannot be established. Accordingly, this can indicate that the durable housing 102 and the base plate 104 have not been connected properly.

In some embodiments, an electrical connection will only be established when the first end 110a contacts the first electrical contact 116a and the second end 110b contacts the third electrical contact 116c. In other embodiments, an electrical connection may be established in a case where the first end 110a and the second end 110b contact the third electrical contact 116c and the first electrical contact 116a respectively. Such embodiments can allow for a detection of a proper connection of the durable housing 102 and the base plate 104 in more than one orientation.

In the embodiment shown in FIG. 3, the shorting mechanism 110 has the first end 110a and second end 110b for contacting the first electrical contact 116a and the third electrical contact 116c, respectively. However, in various other embodiments, the shorting mechanism 110 can be provided with any suitable number of ends or contact surfaces for contacting the electrical contacts 116 as required. Similarly, the first end 110a and second end 110b can be arranged on shorting mechanism 110 in any suitable manner. As a further alternative, the shorting mechanism 110 can comprise a piece of wire, or any suitable arrangement of metallic material coupled to the base plate 104 that can cause an electrical short when the base plate 104 is coupled to the durable housing 102.

In the illustrated embodiment, the electrical contacts 116 can be provided on the durable housing 102 and the shorting mechanism 110 can be provided on the base plate 104. In other embodiments, the electrical contacts 116 can be provided on the base plate 104 and the shorting mechanism 110 can be provided on the durable housing 102. In further embodiments, each of the durable housing 102 and the base plate 104 can be provided with a shorting mechanism 110 and complementing electrical contacts 116.

In addition or in alternative to the above, in some embodiments, a bias member, such as a spring, or the like, may be provided to bias the shorting mechanism or portion thereof (e.g., first end 110a and second end 110b) toward a first position (e.g., an extended position). As such, shorting mechanism or portion thereof may be moveable toward a second position (e.g., a retracted position), for example, as the durable housing 102 and the base plate 104 are brought together. Thus, while in the second position, an electrical connection may be established between the first electrical contact 116a and the third electrical contact 116c via the shorting mechanism 110 in a similar manner to that previously described.

In various embodiments, the electrical contacts 116 and/or the shorting mechanism 110 may be or otherwise comprise a bias member like that previously described. For example, the electrical contacts 116 and/or the shorting mechanism 110 can be metal springs or the like that may be moveable from the first position to the second position as the durable housing 102 and the base plate 104 are brought together.

With continued reference to FIG. 3, the first magnetic source 112 of the base plate 104 can comprise any suitable source of a magnetic field, including, but not limited to, a ferromagnetic material. The first magnetic source 112 can be coupled to the base plate 104 so as to be spaced a selected distance apart from the first magnetically attractive source 114. The spacing between the first magnetic source 112 and the first magnetically attractive source 114 can aid in the alignment and coupling of the durable housing 102 to the base plate 104. In this regard, the first magnetic source 112 can be positioned on the base plate 104 so as to attract a portion of the durable housing 102, and the first magnetically attractive source 114 can be positioned so as to attract a portion of the durable housing 102, as will be discussed herein. In one example, the first magnetically attractive source 114 can comprise a metal, but could comprise any magnetically attractive material. It should be noted that the use of the first magnetically attractive source 114 is merely exemplary, as the base plate 104 could comprise a second magnet, which could also attract a portion of the durable housing 102. Further, although the first magnetic source 112 and first magnetically attractive source 114 are described herein as attracting portions of the durable housing 102, the first magnetic source 112 and first magnetically attractive source 114 could also oppose portions of the durable housing 102, which could indicate misalignment of the durable housing 102 relative to the base plate 104. In addition, the location of the first magnetic source 112 and first magnetically attractive source 114 on the base plate 104 is merely exemplary.

With reference to FIG. 2, the durable housing 102 can include the electrical contacts 116, a second magnetic source 118, a second magnetically attractive source 120 and a base plate detection system 122. Further, the durable housing 102 can include, among other components, a drive motor, a battery, a threaded drive shaft for the fluid reservoir, and suitable circuitry to control those components. Further detail regarding these components can be found in commonly assigned U.S. Patent Publication No. 2011/0160655, U.S. Patent Publication No. 2011/0160654, U.S. Patent Publication No. 2011/0160666, and U.S. Pat. No. 7,905,868, each of which is incorporated by reference herein.

With continued reference to FIG. 2, generally, the first electrical contact 116a and third electrical contact 116c can have a first electrical state when the base plate 104 is spaced apart from the durable housing 102, and can have a second electrical state when the base plate 104 is coupled to the durable housing 102. In this regard, the electrical contacts 116 can be electrically coupled to the base plate detection system 122, which can supply the electrical contacts 116 with a respective voltage through suitable circuitry. The voltage can be applied to the electrical contacts 116 at predetermined intervals, or could be supplied substantially continuously. In one example, the first electrical contact 116a and third electrical contact 116c can comprise an open circuit, and can be measured or observed to have a generally high voltage signal when the durable housing 102 is not coupled to the base plate 104. When the shorting mechanism 110 contacts the first electrical contact 116a and third electrical contact 116c to complete the circuit, the first electrical contact 116a and third electrical contact 116c can be measured or observed to have a low voltage signal. Thus, the first electrical contact 116a and third electrical contact 116c can serve as interrupt contacts, which can signal contact or an interruption in the contact between the base plate 104 and durable housing 102. The second electrical contact 116b can have a high voltage signal when the durable housing 102 is spaced apart from and coupled to the base plate 104. Therefore, the second electrical contact 116b can serve as a reference contact. The electrical contacts 116 can be in communication with the base plate detection system 122 to enable the base plate detection system 122 to determine if the base plate 104 is coupled to the durable housing 102 based on the voltage signals received from the electrical contacts 116.

In this regard, the base plate detection system 122 can compare the measured or observed voltage from each of the electrical contacts 116 against a preselected threshold voltage. If a first voltage signal from the first electrical contact 116a, a second voltage signal from the second electrical contact 116b and/or a third voltage signal from the third electrical contact 116c is greater than the threshold voltage, then the first voltage signal, second voltage signal and third voltage signals can be considered high voltage signals. If the first voltage signal from the first electrical contact 116a, the second voltage signal from the second electrical contact 116b and/or the third voltage signal from the third electrical contact 116c is less than the threshold voltage, then the first voltage signal, second voltage signal and third voltage signals can be considered low voltage signals. Generally, the threshold voltage can range from about 0.1 volts (V) to about 1.0 volts (V). It should be noted that the comparison of the first voltage signal, second voltage signal and third voltage signal to the threshold voltage is merely exemplary, as the first voltage signal, second voltage signal and third voltage signal could be individual discrete voltage measurements, which could be compared relative to each other or to a ground to determine whether the base plate 104 is coupled to the durable housing 102.

With continued reference to FIG. 2, the durable housing 102 can include the second magnetic source 118. The second magnetic source 118 can comprise any suitable source of a magnetic field, such as a ferromagnetic material, an electromagnet, etc. The second magnetic source 118 can be coupled to the durable housing 102 so that the second magnetic source 118 is aligned with and attracted to the first magnetically attractive source 114 when the durable housing 102 is being coupled to the base plate 104. The attraction between the second magnetic source 118 and the first magnetically attractive source 114 can aid in coupling the durable housing 102 to the base plate 104. The second magnetic source 118 can be spaced a selected distance apart from the second magnetically attractive source 120.

The second magnetically attractive source 120 of the durable housing 102 can comprise a metal, but could comprise any magnetically attractive material. The second magnetically attractive source 120 can be coupled to the durable housing 102 so that the second magnetically attractive source 120 can be coupled to the first magnetic source 112 when the durable housing 102 is coupled to the base plate 104. The attraction between the first magnetic source 112 and the second magnetically attractive source 120 can also aid in the alignment and coupling of the durable housing 102 to the base plate 104.

It should be noted that the use of the second magnetically attractive source 120 is merely exemplary, as the durable housing 102 could comprise a second magnet, which could also attract a portion of the base plate 104. Further, although the second magnetic source 118 and second magnetically attractive source 120 are described herein as attracting portions of the base plate 104, the second magnetic source 118 and second magnetically attractive source 120 could also oppose portions of the base plate 104, which could indicate misalignment of the durable housing 102 relative to the base plate 104. In addition, although the durable housing 102 and base plate 104 are described and illustrated herein as each including a respective magnetic source and magnetically attractive material, one of the durable housing 102 and base plate 104 can include magnetic sources and the other of the durable housing 102 and base plate 104 can include the magnetically attractive materials to facilitate coupling the base plate 104 to the durable housing 102. Moreover, the location of the second magnetic source 118 and second magnetically attractive source 120 on the durable housing 102 is merely exemplary.

Figure 4:
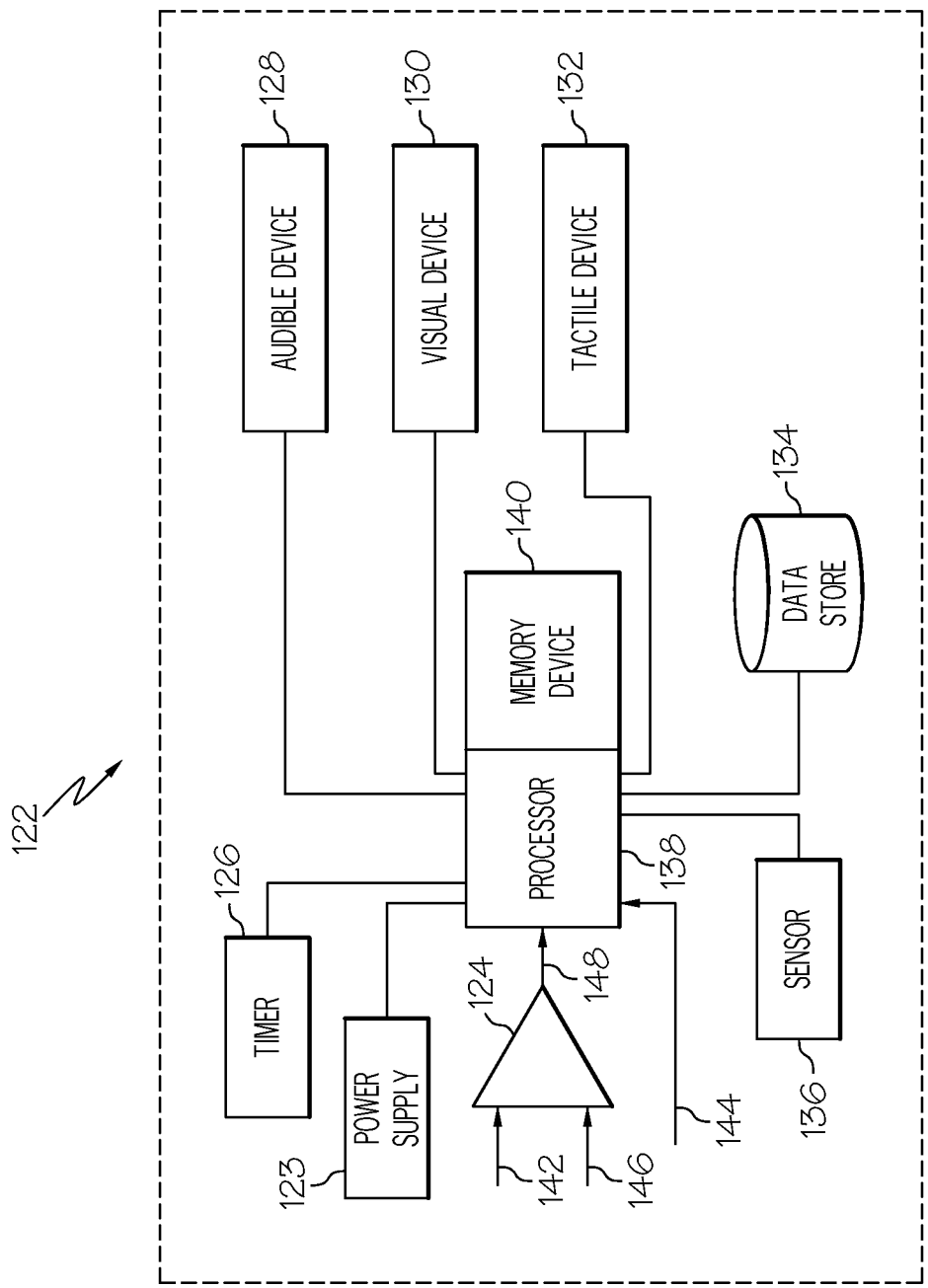
FIG. 4 is a functional block diagram illustrating a base plate detection system in accordance with an exemplary embodiment.

With reference to FIG. 4, a functional block diagram illustrates an exemplary base plate detection system 122 according to one of various embodiments. The base plate detection system 122 can determine if the base plate 104 is properly coupled to the durable housing 102. In this exemplary embodiment, the base plate detection system 122 can include a power supply 123, a comparator circuit 124, a timer 126, an audible device 128, a visual device 130, a tactile device 132, a data store 134, at least one sensor 136, a processor 138 and a memory device 140. It should be noted that although the base plate detection system 122 is described and illustrated herein as being associated with the durable housing 102, the base plate detection system 122 can be associated with the base plate 104, if desired.

With continued reference to FIG. 4, the power supply 123 can supply power to one or more components of the base plate detection system 122 and durable housing 102. In one example, the power supply 123 can be in communication with the processor 138 to supply a voltage to the electrical contacts 116. The power supply 123 can comprise any suitable power source, including, but not limited to, a battery. It should be noted that although the power supply 123 is described and illustrated herein as being separate and discrete from the processor 138, the power supply 123 can be integral with the processor 138 if desired.

The comparator circuit 124 can be in communication with the electrical contacts 116 of the durable housing 102. In one example, the comparator circuit 124 can receive as input a first voltage signal 142 of the first electrical contact 116*a* and a third voltage signal 146 of the third electrical contact 116*c*. Based on the first voltage signal 142 and the third voltage signal 146, the comparator circuit 124 can output a fourth voltage signal 148 for the processor 138. The fourth voltage signal 148 can comprise an indication as to whether the shorting mechanism 110 has contacted the first electrical contact 116*a* and third electrical contact 116*c*. As will be discussed herein, the fourth voltage signal 148 can be used as an interrupt signal and can be compared against a second voltage signal 144 of the second electrical contact 116*b*, which can serve as a reference signal, to determine if the base plate 104 is coupled to the durable housing 102.

The timer 126 can comprise any suitable device capable of timing events. The timer 126 can comprise suitable logic and circuitry for timing events as is generally known in the art. The timer 126 can be in communication with the processor 138. Although the timer 126 is illustrated and described herein as being separate and discrete from the processor 138, the timer 126 could be integrated into the processor 138, if desired.

The audible device 128 can be in communication with the processor 138, and can enable an audible alert to be broadcast to the user upon coupling of the base plate 104 to the durable housing 102. The audible device 128 can comprise any suitable technology for broadcasting audible information, such as a speaker. It should be noted that although the audible device 128 is illustrated herein as being internal to the durable housing 102, the audible device 128 can also be an external speaker coupled to or in communication with the durable housing 102, such as a speaker on a hand held blood glucose meter, for example.

The visual device 130 can be in communication with the processor 138, and can enable a visual alert to be displayed to the user upon coupling of the base plate 104 to the durable housing 102. The visual device 130 can comprise any suitable technology for displaying visual information, such as one or more light emitting diodes (LEDs), one or more organic light emitting diode (OLEDs), a liquid crystal display (LCD) display, a plasma display, or a cathode ray tube (CRT) display. It should be noted that although the visual device 130 is illustrated herein as being coupled to the durable housing 102, the visual device 130 can also be an external visual output or display coupled to or in communication with the durable housing 102, such as a display on a hand held blood glucose meter, for example.

The base plate detection system 122 can also include the tactile device 132, which can be in communication with the processor 138. The tactile device 132 can output a tactile alert to the user upon coupling of the base plate 104 to the durable housing 102. An exemplary tactile alert can comprise a vibration. In one example, the tactile device 132 can comprise any suitable technology for generating a vibration, such as a motor that drives a gear having an offset weight as known in the art. Further, although the tactile device 132 is illustrated herein as being internal to the durable housing 102, the tactile device 132 can also be an external tactile output device coupled to or in communication with the durable housing 102, such as a tactile output device associated with a hand held blood glucose meter, for example.

The data store 134 can be in communication with the processor 138 to store data. Although the data store 134 is illustrated and described herein as being separate and discrete from the memory device 140, the data store 134 can be part of the memory device 140, if desired. The data store 134 can store at least one look-up table, which can be accessed by the processor 138 to assist in determining if the base plate 104 is coupled to the durable housing 102.

The sensor 136 can comprise any suitable sensor that can observe a magnetic field emitted by the first magnetic source 112 and generate sensor signals based on the observed conditions. In one example, the sensor 136 can comprise a single sensor, which can detect the strength and direction of the magnetic field generated by the first magnetic source 112. For example, the sensor 136 can comprise a magnetic angle sensor, however, the sensor 136 can include, but is not limited to, a reed switch or a Hall effect sensor. In this example, the sensor 136 can observe the magnetic field emitted by the first magnetic source 112 that is incident on a central plane of the sensor 136 and can generate sensor signals based on the angle of the magnetic field relative to the sensor 136. In one embodiment, the sensor 136 can have two bridges, for example, Wheatstone bridges, which can be used to observe the angle of the magnetic field. Generally, the sensor signals can be converted to analog-to-digital counts (ADC), which can be read and interpreted by the processor 138. It should be noted that the use of ADC is merely exemplary, as the processor 138 could read and interpret analog signals from the sensor 136, if desired.

The processor 138 according to one of various embodiments can execute one or more programs (i.e., running software) to perform various tasks or instructions encoded in the program(s). The processor 138 can be a microprocessor, microcontroller, application specific integrated circuit (ASIC) or other suitable device as realized by those skilled in the art. Of course, the durable housing 102 can include multiple processors 138, working together or separately, as is also realized by those skilled in the art. The processor 138 can also be in communication with the second electrical contact 116b to receive the second voltage signal 144.

The memory device 140 is capable of storing data. The memory device 140 can be random access memory (RAM), read-only memory (ROM), flash memory, a memory disk (e.g., a floppy disk, a hard disk, or an optical disk), or other suitable device as realized by those skilled in the art. In the illustrated exemplary embodiment, the memory device 140 can be in communication with the processor 138 and stores the program(s) executed by the processor 138. Those skilled in the art realize that the memory device 140 can be an integral part of the processor 138. Furthermore, those skilled in the art realize that the durable housing 102 can include multiple memory devices 140.

Figure 5:
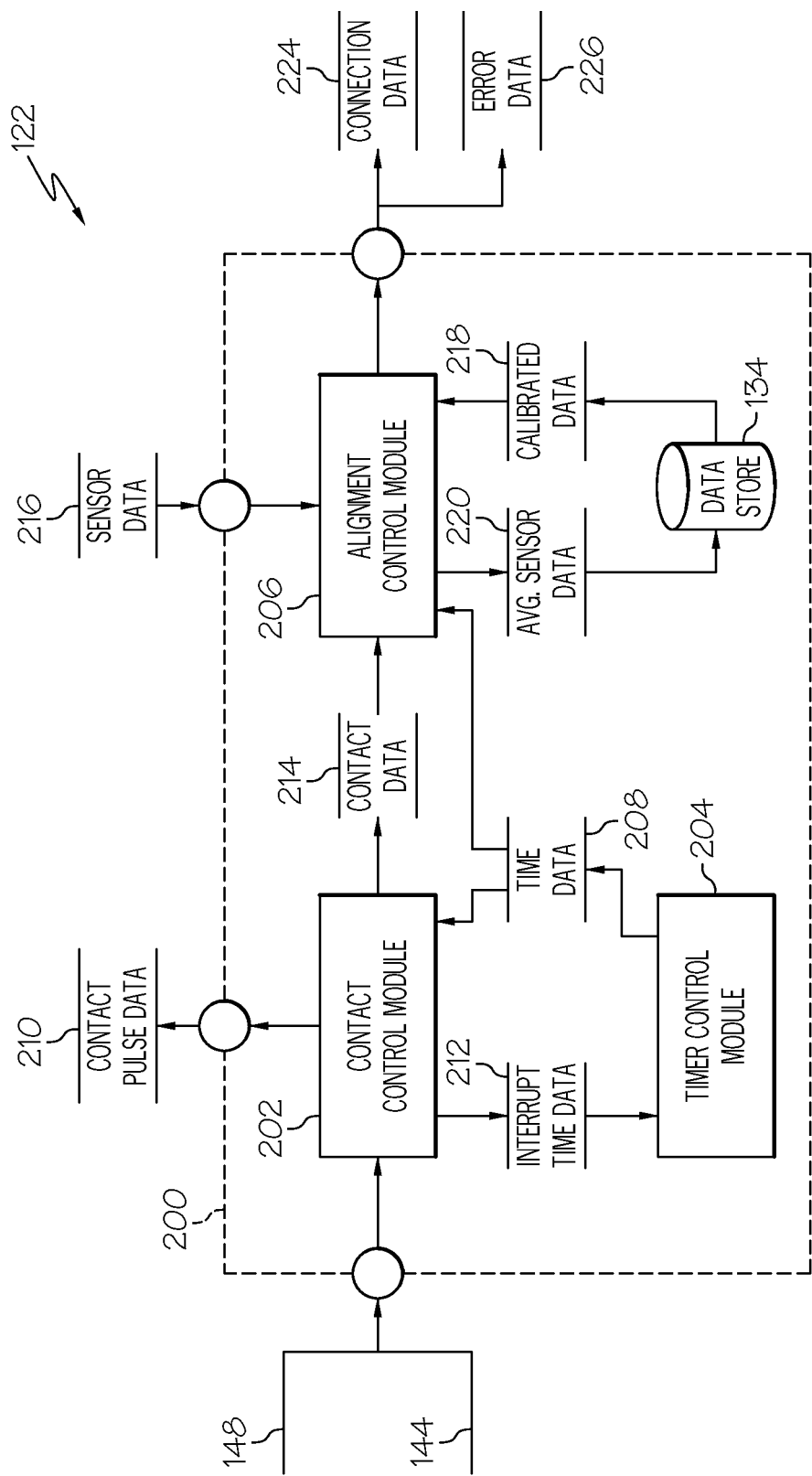
FIG. 5 is a dataflow diagram illustrating a control system of the base plate detection system in accordance with an exemplary embodiment.

Referring now to FIG. 5, a dataflow diagram illustrates various embodiments of the base plate detection system 122 that may be embedded within a control module 200 and performed by the processor 138 (FIG. 4). Various embodiments of the base plate detection system 122 according to the present disclosure can include any number of sub-modules embedded within the control module 200. As can be appreciated, the sub-modules shown in FIG. 5 can be combined and/or further partitioned to determine whether the base plate 104 is coupled to the durable housing 102. Inputs to the system may be sensed by the durable housing 102 (FIG. 1), received from other control modules (not shown), and/or determined/modeled by other sub-modules (not shown) within the control module 200. In various embodiments, the control module 200 can include a contact control module 202, a timer control module 204, and an alignment control module 206.

The contact control module 202 can receive as input the fourth voltage signal 148, the second voltage signal 144 and time data 208. Based on the fourth voltage signal 148, the second voltage signal 144 and the time data 208, the contact control module 202 can output contact pulse data 210. In addition, based on the fourth voltage signal 148, the second voltage signal 144 and the time data 208, the contact control module 202 can set interrupt time data 212 for the timer control module 204 and contact data 214 for the alignment control module 206. The time data 208 can comprise an amount of time that has passed since the initial contact between the durable housing 102 and base plate 104. In other words, the time data 208 can comprise the amount of time that has passed since at least one of the first voltage signal 142 and the third voltage signal 146 changed state (e.g. from a high voltage signal to a low voltage signal or a low voltage signal to a high voltage signal). The contact pulse data 210 can comprise a signal to transmit a voltage pulse to the electrical contacts 116. The voltage pulse can be used to confirm that the base plate 104 is coupled to the durable housing 102.

In this regard, upon receipt of the voltage pulse, the state of the fourth voltage signal 148 and second voltage signal 144 can be detected by the contact control module 202. Based on the state of the fourth voltage signal 148 and second voltage signal 144 after the voltage pulse, the contact control module 202 can determine if the shorting mechanism 110 of the base plate 104 has made contact with the selected electrical contacts 116 of the durable housing 102. The contact data 214 can comprise data that indicates whether electrical contact has been made between the durable housing 102 and base plate 104. The contact data 214 can be obtained from a look-up table stored on the data store 134 and accessed by the contact control module 202 based on the fourth voltage signal 148 and second voltage signal 144, if desired. The interrupt time data 212 can comprise a signal to the timer control module 204 to start a timer. The timer can measure the amount of time that has passed since the initial contact between the durable housing 102 and the base plate 104. The timer control module 204 can receive as input the interrupt time data 212. Based on the interrupt time data 212, the timer control module 204 can set the time data 208.

The alignment control module 206 can receive as input the contact data 214, time data 208, sensor data 216 and calibrated data 218. The sensor data 216 can comprise data from the sensor 136. For example, the sensor data 216 can include the strength and/or direction of a magnetic field. In one example, the sensor data 216 can comprise an angle of the magnetic field relative to the sensor 136. The calibrated data 218 can comprise data that can indicate if the sensor data 216 has observed a magnetic field based on calibrated sensor data, which can be obtained from a look-up table stored in the data store 134.

In this regard, the output of the sensor 136 can be affected by several factors. The calibrated sensor data can include original calibration data for the sensor 136 based on observations of the sensor 136 in response to a magnetic field in a controlled environment, such as during the manufacture of the sensor 136, and can also include stored calibration data for the sensor 136 based on observations of the sensor 136 in response to a magnetic field when the sensor 136 is affected by certain environmental conditions, such as, temperature. As will be discussed, the sensor data 216 can be compared to the calibrated sensor data to determine if the magnetic field is present, which can be set as calibrated data 218.

Based on the contact data 214, time data 208, sensor data 216 and calibrated data 218, the alignment control module 206 can set average sensor data 220 for the data store 134, and can output connection data 224 and error data 226. The average sensor data 220 can comprise an average of the sensor data 216 obtained from the sensor 136 a preselected number of times. For example, the sensor 136 can be sampled from about 5 to about 20 times and the sensor data 216 obtained each time can be averaged to generate the average sensor data 220. Based on the average sensor data 220, the alignment control module 206 can access the look-up table in the data store 134 to compare the average sensor data 220 to calibrated sensor data. In one example, the sensor data 216 can indicate that a magnetic field is present if one bridge of the sensor 136 generates signals between about 100 and about 200 ADC and the other bridge of the sensor 136 generates signals between about 400 and about 800 ADC, which are acceptable ranges for sensor data 216 when a magnetic field is present based on the calibrated sensor data.

The connection data 224 can include data that indicates whether the base plate 104 is coupled to the durable housing 102, which can be output to one or more of the audible device 128, visual device 130 and tactile device 132, if desired. The error data 226 can include data to notify the user that the base plate 104 is not coupled to the durable housing 102, which can be output to one or more of the audible device 128, visual device 130 and tactile device 132.

Figure 6:
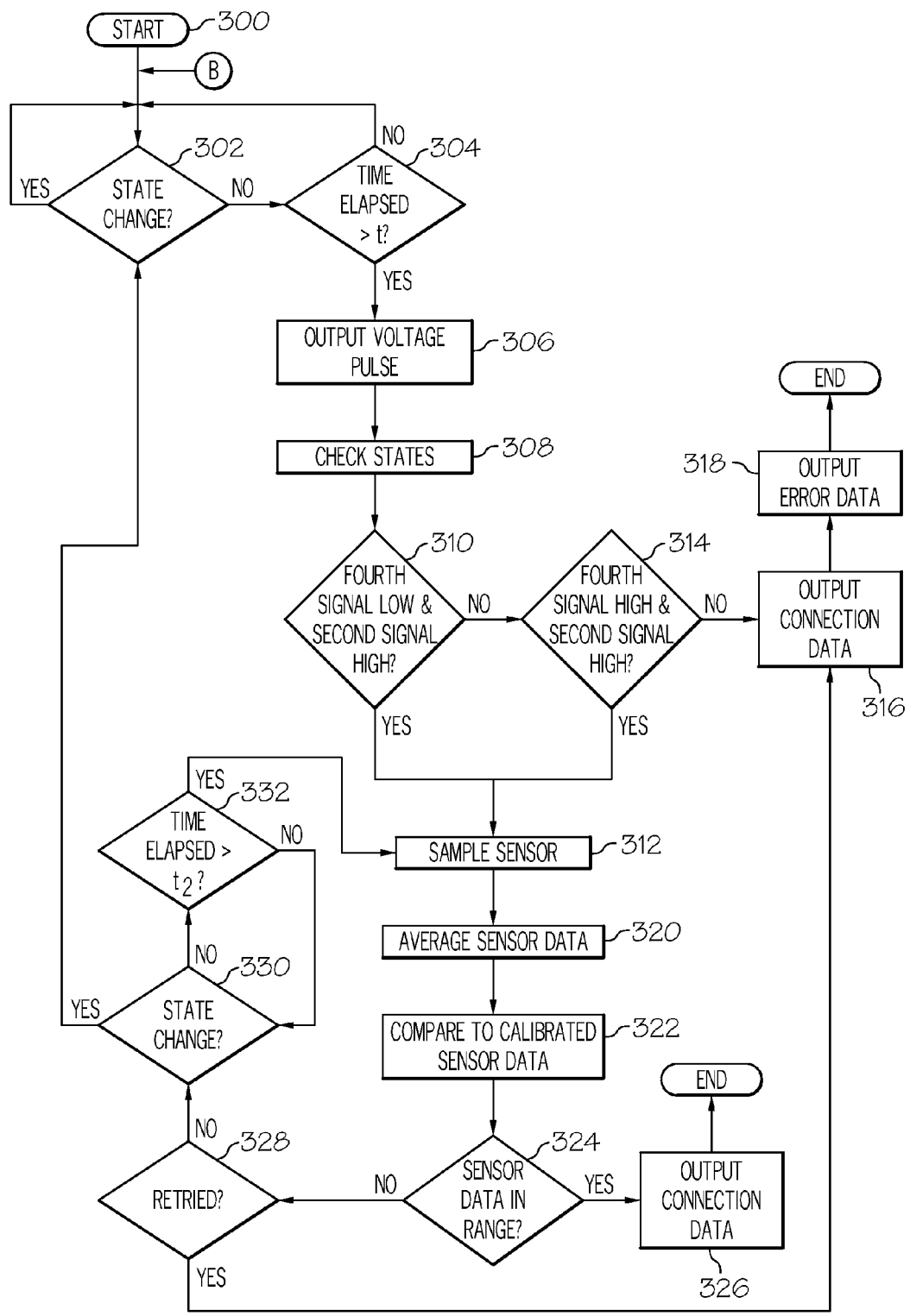
FIG. 6 is a flowchart illustrating a control method of the base plate detection system in accordance with an exemplary embodiment.

Referring now to FIG. 6, and with continued reference to FIGS. 1-5, a flowchart illustrates a control method that can be performed by the control module 200 of FIG. 5 in accordance with the present disclosure. As can be appreciated in light of the disclosure, the order of operation within the method is not limited to the sequential execution as illustrated in FIG. 6, but may be performed in one or more varying orders as applicable and in accordance with the present disclosure.

In various embodiments, the method can be scheduled to run based on predetermined events, and/or can run continually during operation of the fluid infusion device 100. In one example, the method of FIG. 6 can run when there is a change in the state of one or more of the electrical contacts 116. For example, the method can run if at least one of the first electrical contact 116a and third electrical contact 116c has changed state from a high voltage signal to a low voltage signal. For the sake of the below description, this will be considered the initial state change. Upon the initial state change, the method can begin at 300.

At 302, the method can determine if the state of at least one of the first electrical contact 116a and third electrical contact 116c has changed from a low voltage signal to a high voltage signal, by checking an output of the comparator circuit 124, for example. If the state of the first electrical contact 116a and third electrical contact 116c has changed, then the method can loop. Otherwise, the method can go to 304. At 304, the method can determine if the time elapsed since the initial state change is greater than a predetermined time constant t. For example, t can range from about 50 milliseconds to about 150 milliseconds. If the time elapsed is greater than t, then the method can go to 306. Otherwise, the method can loop to 302. Thus, 304 can ensure that the fourth voltage signal from the comparator circuit 124 is stable, and can act as a debounce check for the shorting mechanism 110 of the base plate 104.

At 306, the method can output the contact pulse data 210, which can include a voltage pulse, to the electrical contacts 116. The voltage pulse can be output over a specified duration of time, such as about 0.5 milliseconds to about 2 milliseconds. At 308, the method can check the state of the fourth voltage signal 148 and second voltage signal 144. At 310, the method can determine if the fourth voltage signal 148 is a low voltage signal and the second voltage signal 144 is a high voltage signal. If the fourth voltage signal 148 is a low voltage signal and the second voltage signal 144 is a high voltage signal, the method can go to 312. Otherwise, at 314, the method can determine if the fourth voltage signal 148 is a high voltage signal and the second voltage signal 144 is a high signal. If the fourth voltage signal 148 is a high voltage signal and the second voltage signal 144 is a high voltage signal, then the method can go to 312. Otherwise, the method can go to 316. At 316, the method can output the connection data 224, which can indicate that the base plate 104 is not coupled to the durable housing 102. At 318, the method can output error data 226 to one or more of the audible device 128, visual device 130 and tactile device 132 to notify the user that the base plate 104 is not coupled to the durable housing 102. Then, the method ends.

At 312, the method can sample the sensor 136. In one example, the method can acquire sensor data 216 from the sensor 136 from about 5 to about 20 times. The sensor 136 can be sampled at any given frequency, such as from about 0.5 kilohertz to 1.5 kilohertz. At 320, the method can average the sensor data 216. In one example, the method can average the sensor data 216 using an averaging filter. At 322, the method can access the look-up table stored in the data store 134, and can compare the sensor data 216 to the calibrated data 218 from the look-up table. At 324, the method can determine if the sensor data 216 is within an acceptable range for the sensor data 216 based on the calibrated sensor data. If the sensor data 216 is within the acceptable range, then the method can go to 326. For example, if the first bridge of the sensor 136 generates signals between about 100 and about 200 ADC and the second bridge of the sensor 136 generates signals between about 400 and about 800 ADC, then using the calibrated data 218, the method can determine that the magnetic field is present. Otherwise, the method can go to 328. At 326, the method can output connection data 224, which can indicate that the base plate 104 is coupled to the durable housing 102. The connection data 224 can be output to one or more of the audible device 128, visual device 130 and tactile device 132, if desired. Then, the method ends.

At 328, the method can determine if the sampling of the sensor 136 has already been retried. If the sampling of the sensor 136 has already been retried, then the method goes to 316. Otherwise, at 330, the method can determine if the fourth voltage signal 148 has changed states, from a low voltage signal to a high voltage signal, for example. If the fourth voltage signal 148 has changed states, then the method can go to 302.

Otherwise, at 332, the method can determine based on the time data 208 if the time that has elapsed since the initial state change is greater than a preselected time $t_2$. If the time that has elapsed is greater than the preselected time $t_2$, then the method can go to 312. In one example, the preselected time $t_2$ can range from about 400 milliseconds to 600 milliseconds. Otherwise, the method loops to 330.

Figure 7:
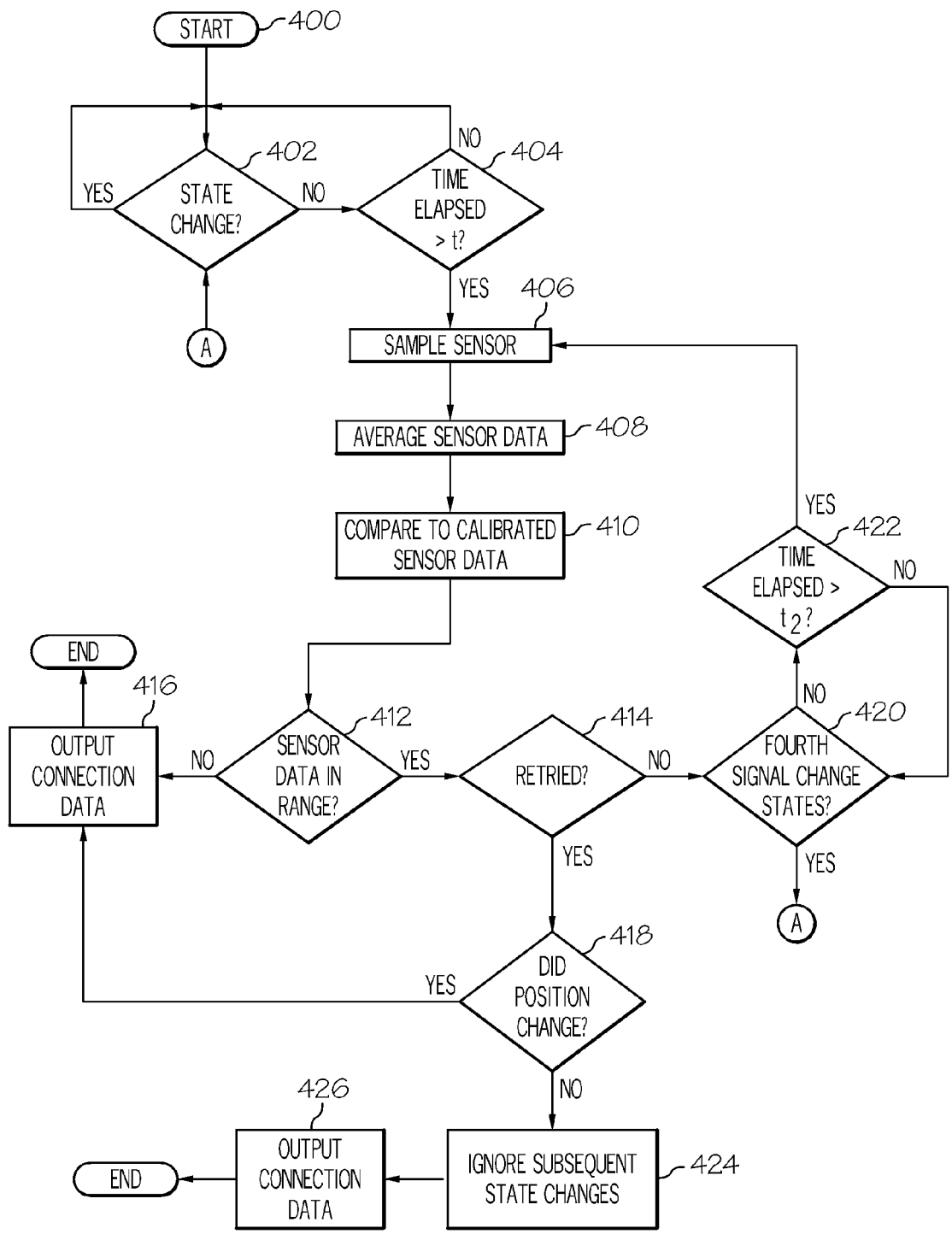
FIG. 7 is a flowchart illustrating a control method of the base plate detection system in accordance with another exemplary embodiment.

Referring now to FIG. 7, and with continued reference to FIGS. 1-5, a flowchart illustrates a control method that can be performed by the control module 200 of FIG. 5 in accordance with the present disclosure. As can be appreciated in light of the disclosure, the order of operation within the method is not limited to the sequential execution as illustrated in FIG. 7, but may be performed in one or more varying orders as applicable and in accordance with the present disclosure.

In various embodiments, the method can be scheduled to run based on predetermined events, and/or can run continually during operation of the fluid infusion device 100. In one example, the method of FIG. 7 can run when the connection data 224 indicates that the base plate 104 is coupled to the durable housing 102 and there is a change in the state of one or more of the electrical contacts 116. For example, the method can run if the base plate 104 is coupled to the durable housing 102 and at least one of the first electrical contact 116a and third electrical contact 116c has changed state from a low voltage signal to a high voltage signal. For the sake of the below description, this will be considered the initial state change. When the base plate 104 is coupled to the durable housing 102, upon the initial state change, the method can begin at 400.

At 402, the method can determine if the state of at least one of the first electrical contact 116a and third electrical contact 116c has changed from a high voltage signal to a low voltage signal, by checking an output of the comparator circuit 124, for example. If the state of the first electrical contact 116a and third electrical contact 116c has changed, then the method can loop. Otherwise, the method can go to 404. At 404, the method can determine if the time elapsed since the initial state change is greater than the predetermined time constant t. If the time elapsed is greater than t, then the method can go to 406. Otherwise, the method can loop to 402. Thus, 404 can ensure that the fourth voltage signal from the comparator circuit 124 is stable, and can act as a debounce check for the shorting mechanism 110 of the base plate 104.

At 406, the method can sample the sensor 136. In one example, the method can acquire sensor data 216 from the sensor 136 from about 5 to about 20 times. The sensor 136 can be sampled at any given frequency, such as from about 0.5 kilohertz to 1.5 kilohertz. At 408, the method can average the sensor data 216. In one example, the method can average the sensor data 216 using an averaging filter. At 410, the method can access the look-up table stored in the data store 134, and can compare the sensor data 216 to the calibrated data 218 from the look-up table. At 412, the method can determine if the sensor data 216 is within an acceptable range for the sensor data 216 based on the calibrated sensor data. If the sensor data 216 is within the acceptable range, then the method can go to 414. Otherwise, the method can go to 416. At 416, the method can output connection data 224, which can indicate that the base plate 104 is not coupled to the durable housing 102. Then, the method ends.

At 414, the method can determine if the sampling of the sensor 136 has already been retried. If the sampling of the sensor 136 has already been retried, then the method goes to 418. Otherwise, at 420, the method can determine if the fourth voltage signal 148 has changed states, from a high voltage signal to a low voltage signal, for example. If the fourth voltage signal 148 has changed states, then the method can go to 402.

Otherwise, at 422, the method can determine based on the time data 208 if the time that has elapsed since the initial state change is greater than the preselected time $t_2$. If the time that has elapsed is greater than the preselected time $t_2$, then the method can go to 406. Otherwise, the method loops to 420.

At 418, the method can determine if the position of the base plate 104 has changed relative to the durable housing 102 based on sensor data 216. In this regard, based on the strength and/or direction of the magnetic field sensed by the sensor 136, the method can determine if the base plate 104 has moved relative to the durable housing 102. For example, when the base plate 104 is coupled to the durable housing 102, one bridge of the sensor 136 can observe and generate signals between about 100 and about 200 ADC and the other bridge of the sensor 136 can observe and generate signals between about 400 and about 800 ADC. If there is a significant change in the signals generated from one or both of the bridges of the sensor 136, along with a state change of at least one of the first electrical contact 116a and third electrical contact 116c, the method can determine that the base plate 104 has moved relative to the durable housing 102. For example, if the signals from one or both of the bridges have changed by about 100 ADC or more, the base plate 104 can be determined to have moved relative to the durable housing 102.

If the base plate 104 has moved, then the method goes to 416. Otherwise, at 424, the method determines to ignore subsequent changes in state of the fourth voltage signal 148 from a low voltage signal to a high voltage signal. At 426, the method outputs the connection data 224, which indicates that the base plate 104 is coupled to the durable housing 102. Then, the method ends.

Figure 8:
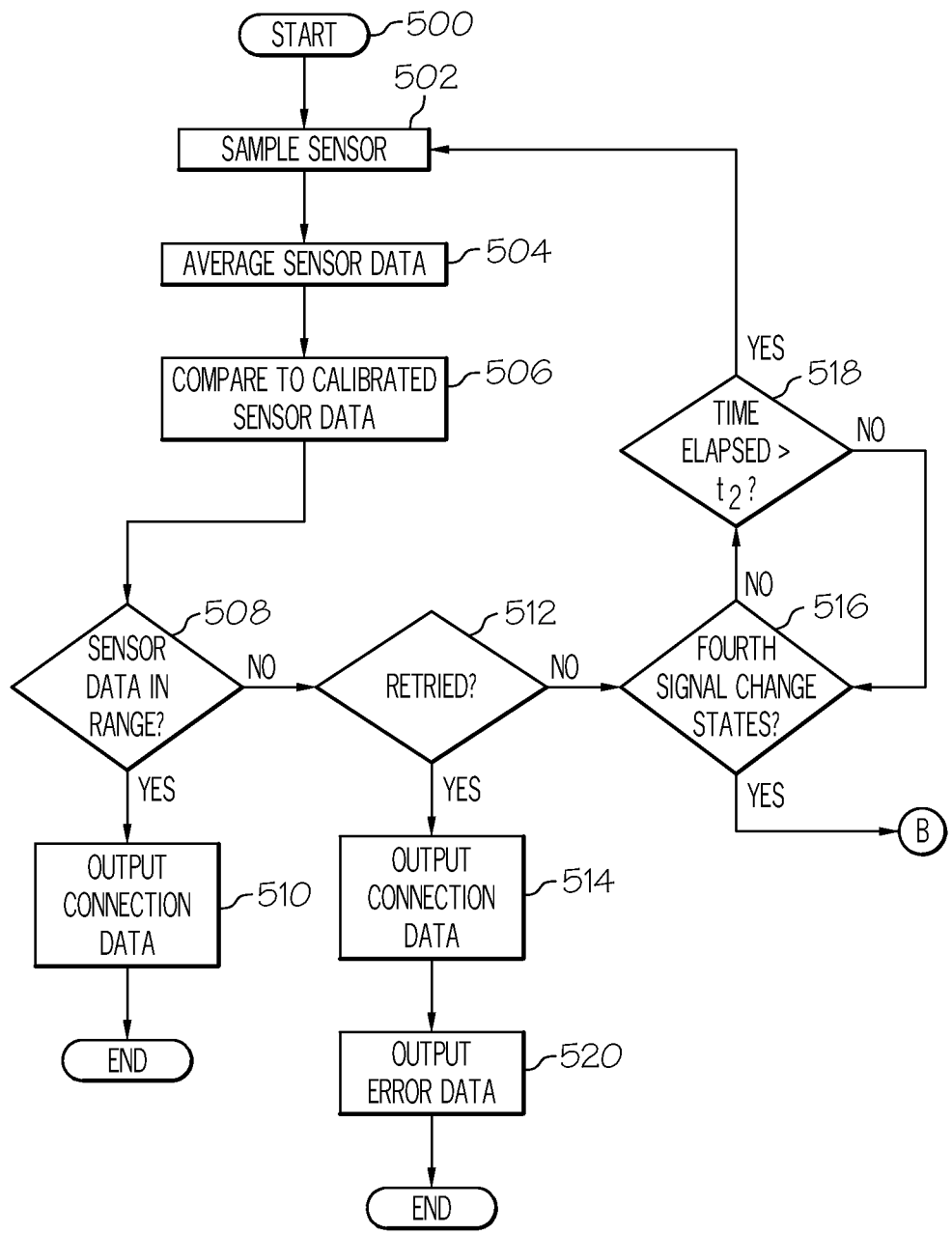
FIG. 8 is a flowchart illustrating a control method of the base plate detection system in accordance with another exemplary embodiment.

Referring now to FIG. 8, and with continued reference to FIGS. 1-5, a flowchart illustrates a control method that can be performed by the control module 200 of FIG. 5 in accordance with the present disclosure. As can be appreciated in light of the disclosure, the order of operation within the method is not limited to the sequential execution as illustrated in FIG. 8, but may be performed in one or more varying orders as applicable and in accordance with the present disclosure.

In various embodiments, the method can be scheduled to run based on predetermined events, and/or can run continually during operation of the fluid infusion device 100. In one example, the method of FIG. 8 can run when the connection data 224 indicates that the base plate 104 is coupled to the durable housing 102 and there is a request to dispense fluid from the fluid reservoir 106. Checking that the base plate 104 is still connected to the durable housing 102 prior to dispensing the fluid from the fluid reservoir 106 can ensure that the user is receiving the fluid. The method can begin at 500.

At 502, the method can sample the sensor 136. In one example, the method can acquire sensor data 216 from the sensor 136 from about 5 to about 20 times. The sensor 136 can be sampled at any given frequency, such as from about 0.5 kilohertz to 1.5 kilohertz. At 504, the method can average the sensor data 216. In one example, the method can average the sensor data 216 using an averaging filter. At 506, the method can access the look-up table stored in the data store 134, and can compare the sensor data 216 to the calibrated data 218 from the look-up table. At 508, the method can determine if the sensor data 216 is within an acceptable range for the sensor data 216 based on the calibrated sensor data. If the sensor data 216 is within the acceptable range, then the method can go to 510. Otherwise, the method can go to 512. At 510, the method can output connection data 224, which can indicate that the base plate 104 is coupled to the durable housing 102. Then, the method ends.

At 512, the method can determine if the sampling of the sensor 136 has already been retried. If the sampling of the sensor 136 has already been retried, then the method goes to 514. Otherwise, at 516, the method can determine if the fourth voltage signal 148 has changed states, from a low voltage signal to a high voltage signal, for example. If the fourth voltage signal 148 has changed states, then the method can go to B on FIG. 6.

Otherwise, at 518, the method can determine based on the time data 208 if the time that has elapsed since the initial state change is greater than the preselected time $t_2$. If the time that has elapsed is greater than the preselected time $t_2$, then the method can go to 502. Otherwise, the method loops to 516.

At 514, the method can output connection data 224, which can indicate that the base plate 104 is not coupled to the durable housing 102. At 520, the method can output error data 226 to one or more of the audible device 128, visual device 130 and tactile device 132 to notify the user that the base plate 104 is not coupled to the durable housing 102. Then, the method ends.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid infusion device for dispersion of a medicine, comprising:
   a consumable component including a source of a magnetic field;
   a durable component including a first electrical contact, a second electrical contact and a third electrical contact, the first electrical contact and third electrical contact having a first electrical state when the consumable component is spaced apart from the durable component and a second electrical state when the consumable component is coupled to the durable component, the durable component including a sensor that observes the magnetic field emitted by the source;

a contact control module that receives a first signal that indicates if the first electrical contact and third electrical contact are in the first electrical state or the second electrical state, and a second signal from the second electrical contact, and based on the first signal and second signal sets contact data that indicates if the consumable component is in contact with the durable component; and an alignment control module that receives the contact data, and based on the contact data samples the sensor to acquire sensor data, and the alignment control module outputs connection data that indicates whether the consumable component is coupled to the durable component based on the contact data and the sensor data.

2. The fluid infusion device of claim 1, further comprising:

a timer control module that generates time data based on an initial contact between the consumable component and durable component, wherein the alignment control module outputs the connection data based on the contact data, time data and the sensor data.

3. The fluid infusion device of claim 1, wherein the alignment control module outputs error data that indicates that the consumable component is not coupled to the durable component based on the contact data and sensor data.

4. The fluid infusion device of claim 1, wherein the alignment control module outputs the connection data to at least one of a visual device, audible device and tactile device.

* * * * *